United States Patent [19]
Alwattari et al.

[11] Patent Number: 5,985,258
[45] Date of Patent: *Nov. 16, 1999

[54] MASCARA COMPOSITIONS COMPRISING WATER-INSOLUBLE POLYMERIC MATERIAL AND WATER-SOLUBLE, FILM-FORMING POLYMERS

[75] Inventors: Ali Abdelaziz Alwattari; Edward Dewey Smith, III, both of Cincinnati, Ohio

[73] Assignee: The Procter & Gamble Company, Cincinnati, Ohio

[ * ] Notice: This patent is subject to a terminal disclaimer.

[21] Appl. No.: 09/121,138

[22] Filed: Jul. 23, 1998

Related U.S. Application Data

[63] Continuation of application No. 08/912,966, Jul. 22, 1997, Pat. No. 5,874,072.

[51] Int. Cl.[6] .................................................. A61K 7/032
[52] U.S. Cl. ................. 424/70.7; 424/70.11; 424/70.16; 424/70.17
[58] Field of Search ................. 424/70.7, 70.11, 424/70.16, 70.17

[56] References Cited

U.S. PATENT DOCUMENTS

| | | | |
|---|---|---|---|
| 3,639,572 | 2/1972 | Heinrich et al. | 424/63 |
| 4,423,031 | 12/1983 | Murui et al. | 424/63 |
| 4,710,374 | 12/1987 | Grollier et al. | 424/61 |
| 4,743,441 | 5/1988 | Takema et al. | 424/47 |
| 5,425,955 | 6/1995 | Narayanan | 424/405 |
| 5,620,693 | 4/1997 | Piot et al. | 424/401 |
| 5,874,072 | 2/1999 | Alwattari et al. | 424/70.7 |

FOREIGN PATENT DOCUMENTS

| | | |
|---|---|---|
| 530084 A1 | 3/1993 | European Pat. Off. . |
| 573229 A2 | 8/1993 | European Pat. Off. . |
| 568035 A2 | 11/1993 | European Pat. Off. . |
| 57-158714 | 9/1982 | Japan . |
| 1-250305 | 10/1989 | Japan . |
| WO 92/21316 | 12/1992 | WIPO . |
| WO 94/17775 | 2/1993 | WIPO . |

OTHER PUBLICATIONS

Cover Girl "Remarkable Washable Waterproof Mascara", Back card of product distributed by Noxell Corporation, A Procter & Gamble Company. Commercially available since 1993.

Clarion "Infinite Lengths Mascara", Back card of product distributed by Noxell Corporation, A Procter & Gamble Company. Commercially available since 1993.

Clarion "Aqualush Waterproof Mascara", Back card of product distributed by Noxell Corporation, A Procter & Gamble Company. Commercially available since 1993.

Max Factor "High Definition Mascara", Back card of product distributed by Max Factor & Co., A Procter & Gamble Company. Commercially available since 1993.

*Primary Examiner*—Jyothsna Venkat
*Attorney, Agent, or Firm*—Darryl C. Little

[57] ABSTRACT

The present invention relates to eye makeup, preferably mascara compositions comprising water-insoluble polymeric materials in the form of an aqueous emulsion and water-soluble, film-forming polymers. Said compositions exhibit improved wear and are removable with soap and water.

12 Claims, No Drawings

5,985,258

MASCARA COMPOSITIONS COMPRISING WATER-INSOLUBLE POLYMERIC MATERIAL AND WATER-SOLUBLE, FILM-FORMING POLYMERS

This application is a continuation of Ser. No. 08/912,966 Jul. 22, 1997, now an U.S. Pat. No. 5,874,072.

TECHNICAL FIELD

The present invention relates to eye make-up compositions, particularly mascaras, comprising water-insoluble polymeric material in the form of an aqueous emulsion and water-soluble, film-forming polymers. Said compositions have improved wear benefits compared to compositions known in the art and are easily removed with soap and water.

BACKGROUND OF THE DISCLOSURE

Eye make-up compositions, including mascara, are significant products in the cosmetics market. Mascara enhances the beauty of the wearer by coating the eye lashes, or in some instances eyebrows, with color.

In spite of their beauty enhancing characteristics, conventional eye make-up preparations have been criticized for their failure to produce the desired effects during long periods of wear. Problems such as staining and smearing, commonly referred to as smudging, and flaking of the mascara from the eyelashes are well known. Even where longevity has been improved, such compositions also are known to be difficult to completely remove from the delicate eye area. An eye makeup composition conceptually having significantly superior wear life, yet, easy removability with soap and water would be very desirable.

Eye makeup compositions comprising polymeric emulsions in order to eliminate smudging are well known in the art and typically include water-insoluble polymers, also referred to as latexes. Such compositions including eye shadows as disclosed in U.S. Pat. No. 3,639,572, Henrich, issued Feb. 1, 1972; and mascaras as disclosed in U.S. Pat. No. 4,423,031. Murui et al., issued Dec. 27, 1983; and European Patent Application (EPA) 0568035, published Nov. 3, 1993. These compositions include plasticizers or solvents to assist in forming films using said latexes. These compositions are known to contain thickeners to adjust the viscosity of the composition. Said thickeners include water-soluble and water-swellable polymers, typically known for such use in the cosmetic art.

In a different embodiment of the above concept is disclosed in Pat. Cooperation Treaty application WO 94/17775, published Aug. 18, 1994. The invention disclosed therein includes mascara compositions comprising water-based silicone elastomeric latex, emulsions as opposed to "water-based" acrylic polymers. Longer wear and durability is attributed to the used of the elastomeric latex as it is more compatible with the rest of the compositional matrix than the acrylic polymers.

Other compositions known in the art which seek to avoid the combination of plasticizers and insoluble-polymer are exemplified in EPO 0530084, published Mar. 3, 1993. This application discloses compositions comprising a dispersed phase and a dispersant phase, the dispersant phase containing at least one water-soluble polymer and the dispersed phase containing at least 50% wax. Said composition may contain other materials routinely used in cosmetic compositions including water-insoluble polymers.

Surprisingly, it has been found that the combination of water-insoluble polymeric materials in an aqueous emulsion and water-soluble, film-forming polymers provides mascara compositions that have superior wear and are removable with soap and water. These mascara compositions can be fabricated in a multitude of forms, such as creams, pastes and solids. Preferably the compositions of the present invention are water-in-oil and oil-in-water emulsions.

SUMMARY OF THE INVENTION

The present invention is for mascara compositions removable with soap and water comprising from about 3% to about 60% water-insoluble polymeric material and from about 2% to about 50% water-soluble, film-forming polymers. All percentages are by weight of the cosmetic composition unless otherwise indicated. All solutions are on a weight/weight concentration unless otherwise indicated.

DETAILED DESCRIPTION OF THE INVENTION

A. Water-insoluble Polymeric Materials

The mascara composition of the present invention comprises water-insoluble polymeric materials in an aqueous emulsion. Said water-insoluble polymeric materials, disclosed in the art as latexes, are aqueous emulsions or dispersions of polymeric materials comprising polymers formed from monomers, said monomer derivatives, mixtures of said monomers, mixtures of said monomer derivatives, natural polymers and mixtures thereof. Said polymeric material also includes chemically modified versions of the above polymers. These water-insoluble polymeric materials of the present invention comprise from about 3% to about 60%; preferably from about 4% to about 40% and most preferably from about 5% to about 30% by weight of the composition.

Water-insoluble polymeric material of the present invention comprise monomers selected from the group consisting of aromatic vinyls, dienes, vinyl cyanides, vinyl halides, vinylidene halides, vinyl esters, olefins and their isomers, vinyl pyrrolidone, unsaturated carboxylic acids, alkyl esters of unsaturated carboxylic acids, hydroxy derivatives of alkyl esters of unsaturated carboxylic acids, amides of unsaturated carboxylic acids, amine derivatives of unsaturated carboxylic acids, glycidyl derivatives of alkyl esters of unsaturated carboxylic acids, olefinic diamines and isomers, aromatic diamines, terephthaloyl halides, olefinic polyols and mixtures thereof. Preferred monomers are selected from the group consisting of aromatic vinyls, dienes, vinyl esters, olefins and their isomers, unsaturated carboxilic acids, alkyl esters of unsaturated carboxylic acids, hydroxy derivatives of alkyl esters of unsaturated carboxylic acids, amides of unsaturated carboxylic acids and mixtures thereof. Most preferred monomers are selected from the group consisting of aromatic vinyls, dienes, vinyl esters, alkyl esters of unsaturated carboxylic acids, hydroxy derivatives of alkyl esters of unsaturated carboxylic acids and mixtures thereof. The polymerization process for making said polymeric material of the present invention is well known in the art. Such processes are disclosed in Kirk Otimer, *Encyclopedia of Chemical Technology*, Volume 14, "Latex Technology" 3rd Ed. 1981; incorporated herein by reference.

Specific polymeric material useful in the present invention include, but, are not necessarily limited to the Syntran Series (of latexes) from Interpolymer Corporation, for example Syntran 5170 and Syntran 5130 (acrylates copolymers formulated with added ammonia, propylene glycol, preservative and surfactant) and Syntran 5002 (styrene/acrylates/methacrylate copolymer formulated with added ammonia, propylene glycol, preservative and surfactant);

the Primal Series (acrylic latexes) from Rohm & Hass; Appretan V (styrene/acrylic ester copolymer latexes) from Hoechst; Vinac (polyvinylacetate latex) from Air Products; UCAR latex resin 130 (polyvinylacetate latex) from Union Carbide; Rhodopas A Series (polyvinylacetate latexes) from Rhone Poulenc; Appretan MB, EM, TV (vinyl acetate/ethylene copolymer latexes) from Hoechst; 200 Series (styrene/butadiene copolymer latexes) from Dow Chemical; Rhodopas SB Series (styrenelbutadiene copolymer latexes) from Rhone Poulenc; Witcobond (polyurethane latexes) from Witco; Hycar Series (butadiene/acrylonitrile copolymer latexes) from Goodrich; Chemigum Series (butadiene/acrylonitrile copolymer latexes) from Goodyear; and Neo Cryl (styrene/acrylates/acrylonitrile copolymer latex) from ICI Resins.

B. Water-soluble, Film Forming Polymers

In addition to the water-insoluble polymeric material disclosed above, the mascara composition of the present invention comprises water-soluble, film forming polymers. Water-soluble, film-forming polymers are defined herein to mean polymers which are soluble in water, water-cosolvent mixtures, such as ethanol/water, pH adjusted water, and/or tempered solutions of the above to facilitate solubilization of the polymers. Water-soluble, film forming polymers comprise from about 2% to about 50%, preferably from about 4% to about 40% and most preferably from about 5% to about 35% of the composition.

The film forming, water-soluble polymers comprise polymers formed from monomers, said monomer derivatives, mixtures of said monomers, mixtures of said monomer derivatives, natural polymers and mixtures thereof. The water-soluble, film forming polymers disclosed herein also include chemically modified versions of the above disclosed polymers. Said monomers are selected from the group consisting of olefin oxides, vinyl pyrrolidone, vinyl esters, vinyl alcohols, vinyl cyanides, oxazilines, carboxylic acids and esters and mixtures thereof. Preferred vinyl pyrrolidone polymers are selected from the group consisting of polyvinylpyrrolidone, vinyl acetate/vinyl pyrrolidone copolymer and mixtures thereof. Preferred polyvinyl esters are selected form the group consisting of vinyl acetate/crotonic acid copolymer, vinyl acetate/crotonic acid/vinyl neodecanoate copolymer and mixtures thereof. Preferred vinyl alcohol polymers are selected from the group consisting of vinyl alcohol/vinyl acetate, vinyl alcohol/poly (alkyleneoxy)acrylate, vinyl alcohol/vinyl acetate/poly-(alkyleneoxy)acrylate and mixtures thereof. Preferred olefin oxides are selected from the group consisting of polyethylene oxide, polypropylene oxide and mixtures thereof. Preferred polycarboxylic acids and their esters are selected from the group consisting of acrylates, acrylates/octylacrylamide copolymers and mixtures thereof. The preferred oxazilines is polyoxazilines.

Water-soluble, film forming polymers of the present invention comprise natural polymers selected from the group consisting of cellulose derivatives, algin and its derivatives, starch and its derivatives, guar and its derivatives, shellac polymers and mixtures thereof. Preferred cellulose derivatives are selected from the group consisting of hydroxyethylcellulose, hydroxypropylcellulose, hydroxypropyl methylcellulose, ethylhydroxyethyl cellulose and mixtures thereof.

Specific water-soluble, film-forming polymers useful in the present invention include, but are not necessarily limited to Polyox WSR (polyethyleneoxide polymers) from Union Carbide; Natrosol 250 (hydroxyethylcellulose) from Aqualon; Cellosize (hydroxyethylcellulose) from Union Carbide; Airvol (polyvinylalcohol copolymer) from Air Products and Chemicals, preferably all commercially available grades like Airvol 103, Airvol 325, Airvol 540, Airvol 523S; Vinex [copolymer of vinyl alcohol and poly(oxyalkylene)acrylate] from Air Products and Chemicals, preferably all commercially available grades such as Vinex 1003, Vinex 2034, Vinex 2144, Vinex 2019; PEOX (polyethyloxazoline) from Polymer Chemistry Innovations; PVP K Series (polyvinylpyrrolidone) from International Specialty Products; Luviskol K Series (polyvinylpyrrolidone) from BASF; PVP/VA (vinyl acetate/vinyl pyrrolidone copolymer) from International Specialty Products, preferably grades W-735 and S-630; and Gantrez (copolymers of methyl vinyl ether/maleic anhydride) from International Specialty Products; Carboset Series (acrylate copolymer) from BF Goodrich; Resyn Series (vinyl acetate/crotonate copolymers) from National Starch and Chemical Corporation; Versatyl and Dermacryl Series (acrylate/octylacrylamide copolymers) from National Starch and Chemical Corporation.

Optional Ingredients

Optional ingredients useful in the present invention are selected based on either the various forms or attributes the composition is to have. The most preferred embodiments of the present invention are water-in-oil or oil-in-water emulsions. Some of the most common optional ingredients include oils and fats, emulsifiers, waxes, pigments and mixtures thereof.

A. Oils and Fats

Mascara compositions of the present invention include oil-in-water or water-in-oil emulsion compositions. These compositions require a lipophilic material or solvent which forms either the dispersed or continuous phases of the composition. Said lipophilic materials typically comprise oils and fats generally known for use in the cosmetic arts.

Oils typically used in cosmetics include those selected from the group consisting of polar oils, non-polar oils, volatile oils, non-volatile oils and mixtures thereof. These oils may be saturated or unsaturated, straight or branched chained, aliphatic or aromatic hydrocarbons. Preferred oils include non-polar volatile hydrocarbons including isodecane (such as Permethyl-99A®, available from Presperse Inc.) and the $C_7$–$C_8$ through $C_{12}$–$C_{15}$ isoparaffins (such as the Isopar® Series available from Exxon Chemicals).

Fats employed according to the invention are selected from the group consisting of fats derived from animals, vegetables, synthetically derived fats, and mixtures thereof wherein said fats have a melting point from about 55° C. to about 100° C. and a needle penetration, as measured according to the American standard ASTM D5, from about 3 to about 40 at 25° C. Preferably the fats selected for use in the present invention are fatty acid esters which are solids at room temperature and exhibit crystalline structure. Examples of fatty acid esters useful in the present invention include the glyceryl esters of higher fatty acids such as stearic and palmitic such as glyceryl monostearate, glyceryl distearate, glyceryl tristearate, palmitate esters of glycerol, $C_{18-36}$ triglycerides, glyceryl tribehenate and mixtures thereof.

B. Emulsifiers

A necessary components in the oil-in-water or water-in-oil emulsion compositions of the present invention are emulsifiers. In these embodiments of the present invention, emulsifiers are typically used at levels from about 0.1% to about 40%, preferably from about 0.5% to about 30%.

There are many factors which determine whether the water or the oil end up the dispersed or continuous phase. However, the single most important factor is the hydrophilic-lipophilic balance value (herein referred to as HLB) of the emulsifier; Wilkinson and Moore, *Harry's Cosmeticology*. 7th Ed. 1982, p. 738. For example Schick and Fowkes, Surfactant Science Series, Vol. 2, *Solvent Properties of Surfactant Solutions*. p 607. Schick and Fowkes discloses that HLB values of surfactant emulsifiers for making water-in-oil emulsions is from 3–6 whereas for making oil-in-water emulsions is from 8–15. Since the emulsions of the present invention includes both types of emulsion mentioned above the emulsifiers selected for use in the present invention are those having an HLB from 3 to about 15. Said emulsifiers include those disclosed in the C.T.F.A. Cosmetic Ingredient Handbook, 1992, pp.587–592; and Remington's Pharmaceutical Sciences, 15th Ed. 1975, pp 335–337; both incorporated herein by reference. Said emulsifiers are selected from those known in the art and mixtures thereof including those in McCutcheon's Volume 1, *Emulsifiers & Detergents*, 1994, North American Edition, pp. 236–239; herein incorporated by reference.

C. Waxes

Waxes are defined as lower-melting organic mixtures or compounds of high molecular weight, solid at room temperature and generally similar in composition to fats and oils except that they contain no glycerides. Some are hydrocarbons, others are esters of fatty acids and alcohols. Waxes useful in the present invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point between 55° and 100° C. and a needle penetration, as measured according to the American standard ASTM D5, of 3 to 40 at 25° C. The principle of the measurement of the needle penetration according to the standards ASTM D5 consists in measuring the depth, expressed in tenths of a millimeter, to which a standard needle (weighing 2.5 g and placed in a needle holder weighing 47.5 g, i.e. a total of 50 g) penetrates when placed on the wax for 5 seconds. Waxes are used at levels in order to provide sufficient bulk material that resists drying out after application, providing thickness to the lashes. Levels of wax commonly found in the art are from about 1% to about 40%.

The specific waxes useful in the present invention are selected from the group consisting of beeswax, lanolin wax, shellac wax (animal waxes); carnauba, candelilla, bayberry (vegetable waxes); ozokerite, ceresin, (mineral waxes); paraffin, microcrystalline waxes (petroleum waxes); polyethylene, (ethylenic polymers); polyethylene homopolymers (Fischer-Tropsch waxes); $C_{24-45}$ alkyl methicones (silicone waxes); and mixtures thereof. Most preferred are beeswax, lanolin wax, carnauba, candelilla, ozokerite, ceresin, paraffins, microcrystalline waxes, polyethylene, $C_{24-45}$ alkyl methicones, and mixtures thereof.

D. Pigments

The solids component of the mascara compositions of the present invention contain cosmetically acceptable pigments selected from the group consisting of inorganic pigments, organic pigments, and pearlescent pigments. When employed, the pigments are present in proportions depending on the color and the intensity of the color which it is intended to produce. The level of pigments in the solid portion of the mascara composition of present invention is from about 3% to about 30%, preferably from about 5% to about 20%. Pigments are selected from the group consisting of inorganic pigments, organic lake pigments, pearlescent pigments, and mixtures thereof. Said pigments may optionally be surface-treated within the scope of the present invention but are not limited to treatments such as silicones, perfluorinated compounds, lecithin, and amino acids.

Inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in the present invention include those selected from the group consisting of D&C Red No. 19 (CI 45,170), D&C Red No. 9 (CI 15,585), D&C Red NO. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No.3 (CI 45,430) and the dye or lakes based on Cochineal Carmine (CI 75,570) and mixtures thereof.

The pearlescent pigments useful in the present invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

E. Miscellaneous

In the present invention numerous optional ingredients may be added to provide additional benefits other than that attributed to the invention as defined above. For example, it is preferred that the mascara composition of the present invention contain a preservative system to inhibit microbiological growth and maintain the integrity of the product. In the present invention, the preservative system does not have a detrimental effect on the composition.

Any optional ingredients known to those skilled in the art may also be used in the invention. Examples of optional ingredients are cosmetic fillers including, but not limited to, mica, talc, nylon, polyethylene, silica, polymethacrylate, kaolin, teflon; cosmetic preservatives including, but not limited to, methylparaben, propylparaben, butylparaben, ethylparaben, potassium sorbate, trisodium EDTA, phenoxyethanol, ethyl alcohol, diazolidinyl urea, imidazolidinyl urea, quatemium-15. Also, additives such as tall oil glycerides are easily incorporated into emulsion forms of the mascara.

Water dispersible and oil dispersible clays may also be useful in the invention to thicken the water or the oil phase. The water dispersible clays comprise bentonite and hectorite, such as Bentone EW, LT from Rheox; magnesium aluminum silicate, such as Veegum from Vanderbilt Co.; attapulgite such as Attasorb or Pharamasorb from Engelhard, Inc.; laponite and montrnorrilonite, such as Gelwhite from ECC America; and mixtures thereof. The oil dispersible clays comprise quatenium-18 bentonite, such as Bentone 34 and 38 from Rheox; the Claytone Series from ECC America; quatemium-18 hectorite, such as Bentone gels from Rheox; and mixtures thereof.

PROCESSING DIRECTIONS

1. Oil-in-Water Emulsion

Place the waxes and fats into a vessel equipped with heating and mixing. Heat the waxes and fats to about 85° C.

with low speed mixing until liquefied and homogeneous. Add pigments, any oil dispersible or soluble components. Increase the mixing rate to high and mix until the pigments are uniformly dispersed throughout the lipid mixture; about 30–35 minutes. Add emulsifiers to said lipid mixture while continuing to mix.

In a second vessel equipped with rnLxing and heating, add water, the water-soluble, film-forming polymers, and the remainder of the water dispersible components. The mixture of water and water-soluble film forming polymers can be made up ahead of the processing of the mascara composition. Mix with heating until this aqueous mixture is about 85° C. Q.S. for any water loss from said aqueous mixture.

Slowly combine the two mixtures and mix with a high speed dispersator type mixer. Remove heat source and continue mixing this combined mixture until the temperature of said combined mixture is from about 65° C.–70° C. Q.S. said combined mixture for any water loss, add the preservatives and insoluble polymer component and mix until homogeneous. Cool said combined mixture to about 45° C.–47° C. and add any remaining components. Continue cooling and mixing until said combined mixture is about 27° C. to about 30° C. Transfer said combined mixture to suitable storage containers for subsequent filling of retail size packaging.

2. Water-in-Oil Emulsions

Combine the lipophilic material and emulsifier in a vessel equipped for mixing. Disperse pigments and any other hydrophobic materials such as fillers into said mixture using a dispersator type mixer. In a separate vessel mix an aqueous solution of the water-soluble, film-forming polymer and the water-insoluble polymeric material emulsion with any water-dispersible ingredients such as preservatives. Slowly combine the two mixtures, continuing to mix at room temperature until the mixture is uniform. Transfer said mixture to suitable storage containers for subsequent filling of retail size packaging.

EXAMPLES

1. Oil-in-Water Mascara

| Ingredient | w/w |
| --- | --- |
| Vinyl acetate/vinyl pyrrolidone copolymer[1] | 38.00 |
| Deionized water | 26.00 |
| Paraffin wax | 7.00 |
| Stearic acid | 9.00 |
| Triethanolamine | 1.50 |
| Iron oxide black | 8.50 |
| Ammonium acrylates copolymer emulsion[2] | 10.00 |
| | 100.00 |

[1]PVP/VA Copolymer W-735 frorn Intemational Specialty Products
[2]Sytran 5170, containing 41% by weight water-insoluble polymer solids, available from Interpolymer Corp.

2. Oil-in-Water Mascara

| Ingredient | w/w |
| --- | --- |
| Copolymer of vinyl alcohol and poly(oxyalkylene)acrylate[1] | 38.19 |
| Deionized water | 11.65 |
| Hectorite[2] | 3.10 |
| Carnauba wax | 1.60 |
| Paraffin wax | 5.90 |
| Beeswax | 3.00 |
| Stearic acid | 2.10 |
| Triethanolamine | 0.70 |

-continued

| Ingredient | w/w |
| --- | --- |
| Petroleum distillate | 4.00 |
| Tall oil glycerides[3] | 2.00 |
| Pentaerythrityl-hydrogenated rosinate[4] | 2.00 |
| Iron oxide black | 10.00 |
| Ammonium acrylates copolymer emulsion[5] | 12.68 |
| Propylene glycol | 1.40 |
| Glycerine | 0.50 |
| Panthenol | 0.28 |
| Preservatives | Q.S. |
| | 100.00 |

[1]Vinex, available from Air Products and Chemicals, incorporated via a 1 6.22 w/w % stock solution in deionized water.
[2]Bentone EW available from Rheox Inc.
[3]Zonester 85 available from Arizona Chemical Co.
[4]Foral 105 available from Hercules Inc.
[5]Syntran 5170, containing 41% by weight water-insoluble polymer solids, available from Interpolymer Corp.

3. Water-in-Oil Mascara

| Ingredient | w/w |
| --- | --- |
| Cyclomethicone[1] | 6.0 |
| Cyclomethicone/Dimethicone Copolyol[2] | 9.0 |
| Silicone Treated Iron Oxide[3] | 12.0 |
| Ammonium acrylates copolymer emulsion[4] | 34.0 |
| Copolymer of vinyl alcohol and poly(oxyalkylene)acrylate[5] | 23.0 |
| Polyethylene[6] | 16.0 |
| | 100.0 |

[1]Dow Coming 244 fluid available from Dow Corning
[2]Dow Coming 3225C, supplied as a solution of dimethicone copolyol in cyclomethicone available from Dow Coming
[3]STNP available from US Cosmetics, Inc.
[4]Syntran 5170 available from Interpolymer Corp.
[5]Vinex, available from Air Products and Chemicals, incorporated via a 20.0 w/w % stock solution in deionized water.
[6]ACumist B6 available from Allied Signal Inc.

We claim:

1. A mascara composition removable with soap and water comprising:
    a. from about 3% to about 60% of water-insoluble polymeric material in an aqueous emulsion wherein the water-insoluble polymeric material comprises a polymer formed from monomers selected from the group consisting of aromatic vinyls, dienes, vinyl cyanides, vinyl halides, vinylidene halides, vinyl esters, olefins and their isomers, vinyl pyrrolidone, unsaturated carboxylic acids, alkyl esters of unsaturated carboxylic acids, hydroxy derivatives of alkyl esters of unsaturated carboxylic acids, amides of unsaturated carboxylic acids, amine derivatives of unsaturated carboxylic acids, glycidyl derivatives of alkyl esters of unsaturated carboxylic acids, olefinic diamines and isomers, aromatic diamines, terephthaloyl halides, olefinic polyols, and mixtures thereof; and
    b. from about 2% to about 50% of water-soluble, film-forming polymer comprising a polymer selected from the group consisting of vinyl alcohol/vinyl acetate copolymer, vinyl alcohol/poly(alkyleneoxy)acrylate copolymer, vinyl alcohol/vinyl acetate/poly(alkyleneoxy)acrylate copolymer and mixtures thereof.

2. A mascara composition according to claim 1 comprising from about 4% to about 40% water-insoluble polymeric material.

3. A mascara composition according to claim 1 comprising from about 5% to about 30% water-insoluble polymeric material.

4. A mascara composition according to claim 1 wherein said water-insoluble polymeric material comprises a polymer formed from monomers selected from the group consisting of aromatic vinyls, dienes, vinyl esters, olefins and their isomers, unsaturated carboxylic acids, alkyl esters of unsaturated carboxylic acids, hydroxy derivatives of alkyl esters of unsaturated carboxylic acids, amides of unsaturated carboxylic acids and mixtures thereof.

5. A mascara composition according to claim 4 wherein said water-insoluble polymeric material comprises a polymer formed from monomers selected from the group consisting of aromatic vinyls, dienes, vinyl esters, alkyl esters of unsaturated carboxylic acids, hydroxy derivatives of alkyl esters of unsaturated carboxylic acids and mixtures thereof.

6. A mascara composition according to claim 1 comprising from about 4% to about 40% water-soluble, film-forming polymers.

7. A mascara composition according to claim 6 comprising from about 5% to about 35% water-soluble, film-forming polymers.

8. A mascara composition according to claim 1 wherein said water-insoluble, polymeric material comprises a polymer selected from the group consisting of acrylates copolymers; styrene/acrylates/methacrylate copolymers; acrylic polymers; styrene/acrylic ester copolymers; polyvinylacetates; vinyl acetate/ethylene copolymers; styrene/butadiene copolymers; polyurethanes; butadiene/acrylonitrile copolymers; styrene/acrylates/acrylonitrile copolymers; and mixtres thereof.

9. A mascara composition according to claim 1 wherein said water-insoluble polymeric material in an aqueous emulsion comprises acrylates copolymer with added ammonia.

10. A mascara composition according to claim 1 wherein said water-soluble, film-forming polymer comprises vinyl alcohol/vinyl acetate copolymer.

11. A mascara composition according to claim 1, further comprising a water-soluble, film-forming polymer selected from the group consisting of (i) polymers formed from monomers, comprising monomers selected fron the group consisting of olefin oxides, vinyl pyrrolidones, vinyl esters, vinyl cyanides, oxazolines, carboxylic acids, carboxylic acid esters and mixture thereof, (ii) polymers formed from a natural polymer selected from the group consisting of cellulose derivatives, algin, starch, guar, shellac polymers and mixtures thereof, and (iii) mixtures thereof.

12. A mascara composition according to claim 11 wherein:

the polymer formed from olefin oxides is selected from the group consisting polyethylene oxide, polypropylene oxide and mixtures thereof;

the polymer formed from vinyl pyrrolidones is selected from the group consisting of polyvinylpyrrolidone, vinyl acetate/vinyl pyrrolidone copolymer and mixtures thereof;

the polymer formed from vinyl esters is selected from the group consisting of vinyl acetate/crotonic acid copolymer, vinyl acetate/crotonic acid/vinyl neodecanoate copolymer and mixtures thereof;

the polymer formed from carboxylic acid esters is selected from the group consisting of acrylates, acrylates/octyl-acrylamide copolymers and mixtures thereof;

the polymer formed from oxazolines is selected from polyoxazolines; and the polymer formed from a natural polymer is selected from the group consisting of hydroxyethylcellulose, hydroxypropylcellulose, hydroxypropyl methylcellulose, ethylhydroxyethyl cellulose and mixtures thereof.

* * * * *